US006355247B1

(12) United States Patent
Selby et al.

(10) Patent No.: US 6,355,247 B1
(45) Date of Patent: *Mar. 12, 2002

(54) NUCLEIC ACID IMMUNIZATION USING A VIRUS-BASED INFECTION/TRANSFECTION SYSTEM

(75) Inventors: Mark Selby, San Francisco; Christopher Walker, Novato, both of CA (US)

(73) Assignee: Chiron Corporation, Emeryville, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/737,061

(22) PCT Filed: May 31, 1995

(86) PCT No.: PCT/US95/06809

§ 371 Date: Nov. 4, 1996

§ 102(e) Date: Nov. 4, 1996

(87) PCT Pub. No.: WO95/33835

PCT Pub. Date: Dec. 14, 1995

Related U.S. Application Data

(63) Continuation-in-part of application No. 08/252,961, filed on Jun. 2, 1994, now abandoned.

(51) Int. Cl.[7] ........................ A61K 39/21; A61K 39/29; C12N 15/863

(52) U.S. Cl. .................. 424/188.1; 424/93.2; 424/93.6; 424/189.1; 424/208.1; 424/228.1; 435/320.1; 435/69.1; 514/44

(58) Field of Search .................. 514/44; 435/172.1, 435/172.3, 320.1, 235.1, 69.1, 455, 456; 424/93.2, 93.6, 188.1, 189.1, 208.1, 228.1

(56) References Cited

U.S. PATENT DOCUMENTS

| | | | |
|---|---|---|---|
| 4,952,496 A | 8/1990 | Studier et al. | 435/91.41 |
| 5,126,251 A | 6/1992 | Moss et al. | 435/69.1 |
| 5,135,855 A | 8/1992 | Moss et al. | 435/69.1 |
| 5,591,601 A | 1/1997 | Wagner et al. | 435/69.1 |

FOREIGN PATENT DOCUMENTS

| | | |
|---|---|---|
| EP | 0 178 863 A1 | 4/1986 |
| WO | WO 90/11092 | 10/1990 |
| WO | WO 93/19092 | 9/1993 |
| WO | WO 94/26911 | 11/1994 |

OTHER PUBLICATIONS

Innes et al., J. Virol., vol. 64, No. 2, pp. 957–961, Feb. 1990.*
Fuerst et al., Molecular and Cellular Biol., vol. 7, No. 7, pp. 2538–2544, Jul. 1987.*
Janis Kuby, "Immunology", Chapter 2, W.H. Freedman and Co., pp. 21–38, 1992.*
B. Moss, In "Current Communications in Molecular Biology" Gene Transfer Vectors for Mammalian Cells; Meeting, Cold Spring Harbor, N.Y., p. 10–14, 1987.*
M.B.A. Oldstone, Virology, vol. 234, 1997, pp. 179–185.*
Rouse et al., Review of Infectious Diseases, vol. 10, No. 1, 1988, pp. 16–33.*
V. Glaser, Genetic Engineering News, Jan. 1, 1996, p. 6.*
Sprent et al., Science, vol. 265, Sep. 1994, pp. 1395–1399.*
J. Cohen, Science, vol. 265, Sep. 1994, pp. 1371–1373.*
Jolly et al., Biotechnology Therapeutics, vol. 2 (1–2), 1991, pp. 179–193.*
Alexander et al., "Regulated Expression of Foreign Genes in Vaccinia Virus under the Control of Bacteriophage T7 RNA Polymerase and the *Escherichia coli lac* Repressor" *J. Virol.* 66(5):2934–2942 (1992).
Chen et al., "A self–initiating eukaryotic transient gene expression system based on cotransfection of bacteriophage T7 RNA polymerase and DNA vectors containing a T7 autogene" *Nuc. Acids Res.* 22(11):2114–2120 (1994).
Deng et al., "Self–amplifying expression from the T7 promoter in 3T3 mouse fibroblasts" *Gene* 143:245–249 (1994).
Dubendorff et al., "Creation of a T7 Autogene: Cloning and Expression of the Gene for Bacteriophage T7 RNA Polymerase under Control of Its Cognate Promoter", *J. Mol. Biol.* (1991) 219:61–68.
Eisenlohr et al., "A transient transfection system for identifying biosynthesized proteins processed and presented to clas I MHC restricted T lymphocytes", *J. Immunol. Meth.* (1992) 154:131–138.
Elroy–Stein and Moss, "Cytoplasmic expression system based on constitutive synthesis of bacteriophage T7 RNA polymerase in mammalian cells", *Proc. Natl. Acad. Sci. USA* (1990) 87:6743–6747.
Elroy–Stein et al., "Cap–independent translation of mRNA conferred by encephalomyocarditis virus 5'sequence improves the performanc of the vaccine virus/bacteriophage T7 hybrid expression system" *Proc. Nat. Acad. Sci. USA* 86:6126–6130 (1989).
Fuerst et al., "Structure and Stability of mRNA Synthesized by Vaccinia Virus–encoded Bacteriophage T7 RNA Polymerase in Mammalian Cells" *J. Mol. Biol.* 206:333–348 (1989).

(List continued on next page.)

Primary Examiner—David Guzo
(74) Attorney, Agent, or Firm—Roberta L. Robins; Alisa A. Harbin; Robert P. Blackburn

(57) ABSTRACT

A method for nucleic acid immunization which results in a cell-mediated immunological response to a selected antigen is disclosed. The method utilizes the T7 RNA infection/transfection system which provides for the controlled, transient cytoplasmic expression of a given antigen and which elicits the production of class I MHC restricted CTLs.

20 Claims, 6 Drawing Sheets

OTHER PUBLICATIONS

Fuerst et al., "Eukaryotic transient–expression system based on recombinant vaccinia virus that synthesizes bacteriophage T7 NRA polymerase", *Proc. Natl. Acad. Sci. USA* (1986) 83:8122–8126.

Gao et al., "Cytoplasmic Gene Expression by Co–delivery of T7 RNA polymerase and T7 Promoter Sequence by Catonic Liposome" *J. Cell. Biochem.* Supp. 17E, p. 206 (1993).

Gao et al., "Cytoplasmic expression of a reporter gene by co–delivery of T7 RNA polymerase and T7 pormoter sequence with cationic liposomes" *Nuc. Acids Res.* 21(12):2867–2872 (1993).

Gao et al., "A Sustained Cytoplasmic Transgene Expression System Delivered by Cationic Liposomes" *Biochem. Biophys. Res. Commun.* 200(3):1201–1206 (1994).

Selby et al., "Expression, identification and subcellular localization of the proteins encoded by the hepatitis C viral genome", *J. Gen. Virol.* (1993) 74:1103–1113.

Studier et al., "Use of T7 RNA Polymerase to Direct Expression of Cloned Genes" in *Gene Expression Technology*, ed. D.V. Goeddel 185:60–89 (1990).

Studier et al., "Use of Bacteriophage T7 RNA Polymerase to Direct Selective High–Level Expression of Cloned Genes" *J. Mol. Biol. 189*:113–130 (1986).

Tang et al., "Genetic immunization is a simple method for eliciting an immune response", *Nature* (1992) 356:152–154.

Tomei et al., "NS3 is a serine protease required for processing of hepatitis C virus polyprotein", *J. Virol.* (1993) 67:4017–4026.

Ulmer et al., "Heterologous protection against influenza by injection of DNA encoding a viral protein", *Science* (1993) 259:1745–1749.

Walker et al. "Cationic Lipids Direct a Viral Glycoprotein into the Class I Major Histocompatibility Complex Antigen––Presentation Pathway," *Proc. Natl. Acad. Sci. USA* (1992) 89:7915–7918.

Wang et al., "Gene inoculation generates immune responses against human immunodeficiency virus type 1", *Proc. Natl. Acad. Sci. USA* (1993) 90:4156–4160.

* cited by examiner

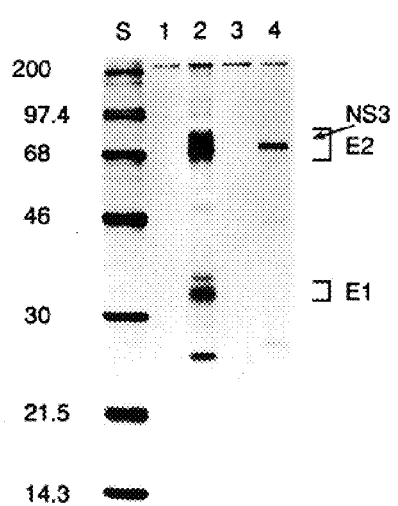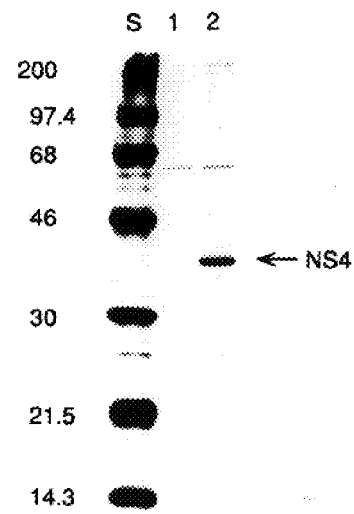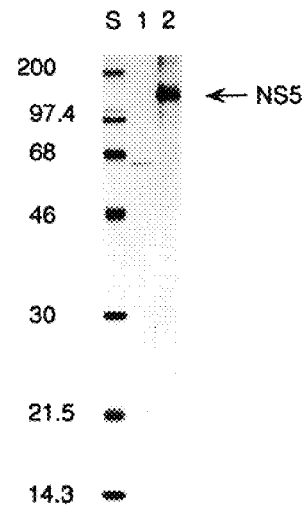

SEQUENCE LISTING

<160> NUMBER OF SEQ ID NOS: 6

<210> SEQ ID NO 1
<211> LENGTH: 9
<212> TYPE: PRT
<213> ORGANISM: Hepatitis C virus

<400> SEQUENCE: 1

Thr Gly Asp Phe Asp Ser Val Ile Asp
 1               5

<210> SEQ ID NO 2
<211> LENGTH: 8
<212> TYPE: PRT
<213> ORGANISM: Hepatitis C virus

<400> SEQUENCE: 2

```
His Pro Asp Ala Thr Tyr Ser Arg
  1               5

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: primer
      p55gag(1)

<400> SEQUENCE: 3

Gly Val Pro Val Trp Lys Glu Ala Thr Thr
  1               5                  10

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: primer
      p55gag(1)

<400> SEQUENCE: 4
aggagagagc catgggtgct g                                          21

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: primer
      p55gag(2)

<400> SEQUENCE: 5
cgcggatcct attgtgacga ggggtcgtt                                  29

<210> SEQ ID NO 6
<211> LENGTH: 10
<212> TYPE: PRT
<213> ORGANISM: Hepatitis C virus

<400> SEQUENCE: 6

Lys His Pro Asp Ala Thr Tyr Ser Arg Cys
  1               5                  10
```

NUCLEIC ACID IMMUNIZATION USING A VIRUS-BASED INFECTION/TRANSFECTION SYSTEM

CROSS-REFERENCE TO RELATED APPLICATION

This application is a continuation-in-part of application Ser. No. 08/252,961 filed Jun. 2, 1994, now abandoned, from which priority is claimed pursuant to 35 USC §120 and which is incorporated herein by reference in its entirety.

BACKGROUND OF THE INVENTION

1. Technical Field

The present invention relates generally to nucleic acid immunization. In particular, the invention relates to an infection/transfection system for nucleic acid immunization which stimulates a cell-mediated immune response in a vertebrate subject.

2. Background of the Invention

Cytotoxic T-lymphocytes (CTLs) play an important role in cell-mediated immune defense against intracellular pathogens such as viruses and tumor-specific antigens produced by malignant cells. CTLs mediate cytotoxicity of virally infected cells by recognizing viral determinants in conjunction with class I MHC molecules displayed by the infected cells. Cytoplasmic expression of proteins is a prerequisite for class I MHC processing and presentation of antigenic peptides to CTLS. However, immunization with killed or attenuated viruses often fails to produce the CTLs necessary to curb intracellular infection. Furthermore, conventional vaccination techniques against viruses displaying marked genetic heterogeneity and/or rapid mutation rates that facilitate selection of immune escape variants, such as the human immunodeficiency virus (HIV) or influenza, are problematic.

Recently, a technique for the direct injection of DNA and mRNA into mammalian tissue, has been described. See, e.g., International Publication No. WO 90/11092 (published Oct. 4, 1990). The method, termed "nucleic acid immunization" herein, has been shown to elicit both humoral and cell-mediated immune responses. For example, sera from mice immunized with a human immunodeficiency virus type 1 (HIV-1) DNA construct encoding the envelope glycoprotein, gp160, were shown to react with recombinant gp160 in immunoassays and lymphocytes from the injected mice were shown to proliferate in response to recombinant gp120. Wang et al. *Proc. Natl. Acad. Sci. USA* (1993) 90:4156–4160. Similarly, mice immunized with a plasmid containing a genomic copy of the human growth hormone (hGH) gene, demonstrated an antibody-based immune response. Tang et al. *Nature* (1992) 356:152–154. Intramuscular injection of DNA encoding influenza nucleoprotein driven by a mammalian promoter has been shown to elicit a CD8+ CTL response that can protect mice against subsequent lethal challenge with virus. Ulmer et al. *Science* (1993) 259:1745–1749. Immunohistochemical studies of the injection site revealed that the DNA was taken up by myeloblasts, and cytoplasmic production of viral protein could be demonstrated for at least 6 months.

However, safety issues limit the usefulness of nucleic acid immunization. In particular, there is the potential for integration of unwanted, foreign DNA into the recipient's genome and the possibility of long-term expression of a protein that is potentially harmful to the host. A possible solution to the latter problem is by employing a system that assures the transient, controlled expression of the administered sequence in the host cell.

A vaccinia based infection/transfection system has been developed (Fuerst et al. *Proc. Natl. Acad. Sci. USA* (1986) 83:8122–8126) which provides for the transient expression of a protein sequence in a host cell. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with a DNA of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation products. See, e.g., Elroy-Stein and Moss, *Proc. Natl. Acad. Sci. USA* (1990) 87:6743–6747. The system has been used to study protein processing and subcellular localization, as well as for the identification of proteins encoded by various viral genomes. See, e.g., Tomei et al. *J. Virol.* (1993) 67:4017–4026; Selby et al. *J. Gen. Virol.* (1993) 74:1103–1113. The system has recently been shown to be useful for the identification of CTL epitopes from influenza gene products. Eisenlohr et al. *J. Immunol. Meth.* (1992) 154:131–138.

However, none of the above-described art provides an infection/transfection method of nucleic acid immunization which allows the transient, cytoplasmic expression of a selected antigen in order to elicit a class I MHC restricted CTL response.

DISCLOSURE OF THE INVENTION

The present invention is based on the discovery of a system for nucleic acid immunization which is effective in eliciting a cell-mediated immune response to a particular antigen. The invention takes advantage of an infection/transfection system which provides for the controlled, transient cytoplasmic expression of a given antigen and which elicits the production of class I MHC restricted CTLS.

Accordingly, in one embodiment, the invention is directed to a method of nucleic acid immunization which results in a cell-mediated immunological response to a selected antigen. The method comprises immunizing a vertebrate subject by:

(a) introducing a source of bacteriophage T7 RNA polymerase into a cell of the subject; and (b) transfecting the cell with a recombinant vector comprising a coding sequence which encodes the selected antigen operably linked to the bacteriophage T7 promoter, wherein the transfecting is done under conditions whereby the coding sequence is transcribed and translated in the cell, thereby resulting in the production of a cell-mediated immunological response in said vertebrate subject.

In particularly preferred embodiments, the T7 polymerase is introduced using a recombinant vaccinia virus, the recombinant vector is liposome-encapsulated and the selected antigen is a viral antigen such as a human immunodeficiency virus (HIV) or a hepatitis C virus (HCV) envelope glycoprotein.

In another embodiment, the invention is directed to a vaccine composition comprising a recombinant vector which includes a coding sequence for a selected antigen operably linked to the bacteriophage T7 promoter, in admixture with a pharmaceutically acceptable excipient.

In yet another embodiment, the invention is directed to a method of making a vaccine composition which comprises admixing a recombinant vector which includes a coding sequence for a selected antigen operably linked to the bacteriophage T7 promoter, with a pharmaceutically acceptable excipient.

These and other embodiments of the subject invention will readily occur to those of skill in the art in light of the disclosure herein.

BRIEF DESCRIPTION OF THE FIGURES

FIG. 2 (PART A–C is a representation of autoradiographs of polyacrylamide gels showing the immunoprecipitation of HCV proteins from infected/transfected chimpanzee fibroblasts. Labeled lysates were immunoprecipitated with the indicated antibody followed by fractionation on 12.5% polyacrylamide gels and autoradiography. In FIG. 2A, F503 monolayers were transfected with pEMCV-βgal (lanes 1 and 3), pEMCV-CE2 (lane 3) or pEMCV-NS25 and labeled lysates were immunoprecipitated with rabbit anti-E2 antibody (lanes 1 and 2) or rabbit anti-NS3 [anti-C33c] (lanes 3 and 4). Envelope glycoprotein E2 (gp68–76 kd) is denoted by a bracket as is E1 (gp32), which was co-immunoprecipitated by E2-specific antibody. NS3 is denoted by an arrow and has a molecular weight of 72 kd. S denotes $^{14}$C-labeled molecular weight standards (BRL); the molecular weights are shown on the left. In FIG. 2B, F503 cells were transfected with no DNA or with pEMCV-NS4 and the labeled lysates were immunoprecipitated with anti-NS4 (anti-C100) antibody. The migration of NS4 is denoted by an arrow. In FIG. 2C, F503 cells were transfected with no DNA or pEMCV-NS5 and the labeled lysates were immunoprecipitated with anti-NS5 antibody. The migration of NS5 (~120 kd) is denoted by an arrow.

DETAILED DESCRIPTION OF THE INVENTION

Figure 1:
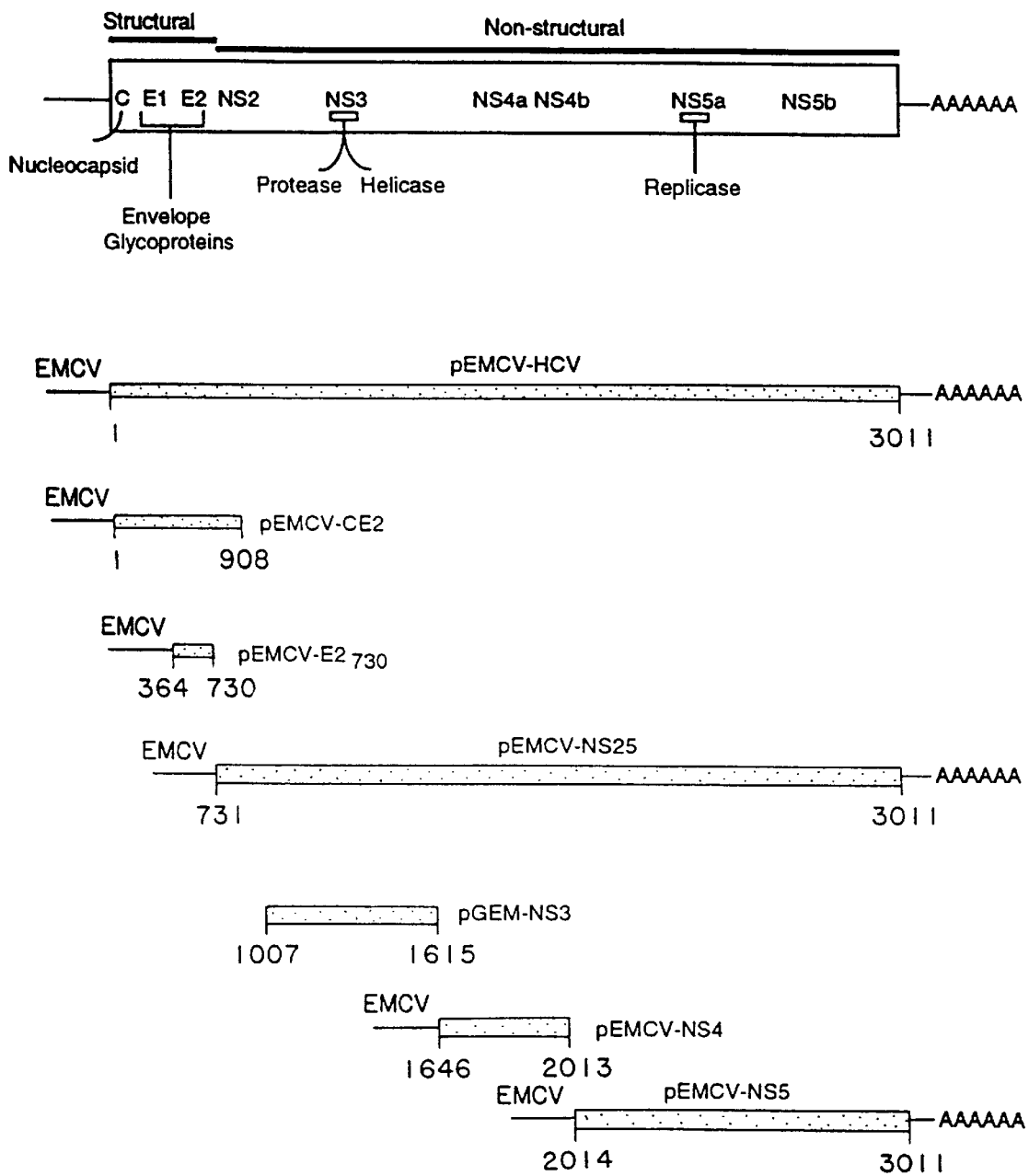
FIG. 1 depicts recombinant HCV cDNA clones used in infection/transfection experiments and the amino acid coordinates of structural and non-structural proteins derived from translation of the full-length HCV polyprotein. EMCV signifies a leader sequence derived from endomylocarditis virus which specifies cap-independent initiation of translation. The A nucleotides at the 3' end of several clones correspond to a polyA tract that consists of 15A residues.

The practice of the present invention will employ, unless otherwise indicated, conventional methods of virology, microbiology, molecular biology and recombinant DNA techniques within the skill of the art. Such techniques are explained fully in the literature. See, e.g., Sambrook, et al. *Molecular Cloning: A Laboratory Manual* (2nd Edition, 1989); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984); *Fundamental Virology*, 2nd Edition, vol. I & II (B. N. Fields and D. M. Knipe, eds.)

As used in this specification and the appended claims, the singular forms "a," "an" and "the" include plural references unless the content clearly dictates otherwise.

I. Definitions

In describing the present invention, the following terms will be employed, and are intended to be defined as indicated below.

By "nucleic acid immunization" is meant the introduction of a nucleic acid molecule encoding one or more selected antigens into a host cell, for the in vivo expression of the antigen or antigens. The nucleic acid molecule can be introduced directly into the recipient subject, such as by injection, inhalation or the like, or can be introduced ex vivo, into cells which have been removed from the host. In the latter case, the transformed cells are reintroduced into the subject where a cell-mediated immune response can be mounted against the antigen encoded by the nucleic acid molecule.

By "antigen" is meant a molecule which contains one or more epitopes that will stimulate a host's immune system to make a cellular antigen-specific immune response when the antigen is expressed using the infection/transfection system herein described. Thus, epitopes within the antigen, when in association with class I MHC molecules at the cell surface, will elicit the generation of CTLS. Normally, an epitope will include between about 7 and 15 amino acids.

For purposes of the present invention, antigens can be derived from any of several known viruses, bacteria, parasites and fungi. The term also intends any of the various tumor antigens. Furthermore, for purposes of the present invention, an "antigen" refers to a protein which includes modifications, such as deletions, additions and substitutions (generally conservative in nature), to the native sequence, so long as the protein maintains the ability to elicit a cell-mediated immune response when expressed using the subject infection/transfection system. These modifications may be deliberate, as through site-directed mutagenesis, or may be accidental, such as through mutations of hosts which produce the antigens.

An "immunological response" to a composition or vaccine, as used herein, is the development in the vertebrate subject of a cellular immune response to the composition or vaccine of interest. Thus, an "immunological response" for purposes of the present invention will be one which serves to sensitize a vertebrate subject by the presentation of the antigen of interest at the cell surface, in association with class I MHC molecules. In this way, CTLs can be generated against the presented molecule to allow for the future protection of an immunized host. The presence of a cell-mediated immunological response may be determined using CTL cytotoxic cell assays, well known in the art, such as the assay described in Erickson et al. *J. Immunol.* (1993) 151:4189–4199 and as described further below in the examples.

The antigen of interest may also elicit an antibody-mediated immune response. Thus, an immune response as used herein will be one which stimulates the production of CTLs but can also include one or more of the following effects; the production of antibodies, B cells, helper T cells, suppressor T cells, and/or γδ T cells, directed specifically to an antigen or antigens encoded by the nucleic acid molecule included in the composition or vaccine of interest. These responses may serve to neutralize infectivity, and/or mediate antibody-complement or antibody dependent cell cytotoxicity to provide protection to an immunized host.

A "coding sequence" or a sequence which "encodes" a selected antigen, is a nucleic acid sequence which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence.

A "nucleic acid" sequence can include, but is not limited to, procaryotic sequences, eucaryotic mRNA, cDNA from eucaryotic mRNA, genomic DNA sequences from eucaryotic (e.g., mammalian) DNA, and even synthetic DNA sequences. The term also captures sequences that include any of the known base analogs of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

"Operably linked" refers to an arrangement of elements wherein the components so described are configured so as to perform their usual function. Thus, a T7 promoter operably linked to a coding sequence is capable of effecting the expression of the coding sequence when T7 RNA polymerase is present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Recombinant" as used herein to describe a nucleic acid molecule means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide.

Two nucleic acid or polypeptide sequences are "substantially homologous" when at least about 80% (preferably at least about 90%, and most preferably at least about 95%) of the nucleotides or amino acids match over a defined length of the molecule. As used herein, substantially homologous also refers to sequences showing identity to the specified nucleic acid or polypeptide sequence. Nucleic acid sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, vols I & II, supra; *Nucleic Acid Hybridization*, supra.

A "vector" is a replicon in which a heterolo-gous polynucleotide segment is attached, so as to bring about the replication and/or expression of the attached segment, such as a plasmid, transposon, phage, etc.

As used herein, "treatment" refers to any of (i) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

By "vertebrate subject" is meant any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The system described above is intended for use in any of the above vertebrate species, since the immune systems of all of these vertebrates operate similarly.

II. Modes of Carrying Out the Invention

The present invention is based on the development of a method for nucleic acid immunization which results in cell-mediated immunity. The system takes advantage of the highly specific bacteriophage T7 promoter. In particular, constructs are provided which include a coding sequence for a selected antigen, driven by this promoter. Thus, in the presence of T7 polymerase, large quantities of the antigen are produced, resulting in enhanced immunogenicity. Furthermore, the gene encoding the antigen is only expressed so long as T7 polymerase is present, thus providing a mechanism for the controlled, transient expression of the gene. Accordingly, potentially harmful side effects associated with long-term, constitutive expression of a particular protein, are avoided.

As explained above, the system herein described provides for the association of the expressed antigens with class I MHC molecules such that an in vivo cellular immune response to the antigen of interest can be mounted which stimulates the production of CTLs to allow for future recognition of the antigen. Accordingly, the methods of the present invention will find use with any antigen for which a cellular immune response is desired, including antigens derived from viral, bacterial, fungal and parasitic pathogens that may induce antibodies, T-cell helper epitopes and T-cell cytotoxic epitopes. Such antigens include those encoded by human and animal viruses and can correspond to either structural or non-structural proteins. Both secreted and cell-localized proteins can also be expressed using the present system.

The technique is particularly useful for immunization against intracellular viruses and tumor cell antigens which normally elicit poor immune responses. For example, the present invention will find use for stimulating an immune response against a wide variety of proteins from the herpesvirus family, including proteins derived from herpes simplex virus (HSV) types 1 and 2, such as HSV-1 and HSV-2 glycoproteins gB, gD and gH; antigens derived from varicella zoster virus (VZV), Epstein-Barr virus (EBV) and cytomegalovirus (CMV) including CMV gB and gH; and antigens derived from other human herpesviruses such as HHV6 and HHV7. (See, e.g. Chee et al. *Cytomegaloviruses* (J. K. McDougall, ed., Springer-Verlag 1990) pp. 125–169, for a review of the protein coding content of cytomegalovirus; McGeoch et al. *J. Gen. Virol.* (1988) 69:1531–1574, for a discussion of the various HSV-1 encoded proteins; U.S. Pat. No. 5,171,568 for a discussion of HSV-1 and HSV-2 gB and gD proteins and the genes encoding therefor; Baer et al. Nature (1984) 310:207–211, for the identification of protein coding sequences in an EBV genome; and Davison and Scott, *J. Gen. Virol.* (1986) 67:1759–1816, for a review of VZV.)

Polynucleotide sequences encoding antigens from the hepatitis family of viruses, including hepatitis A virus (HAV), hepatitis B virus (HBV), hepatitis C virus (HCV), the delta hepatitis virus (HDV) and hepatitis E virus (HEV), can also be conveniently used in the techniques described herein. By way of example, the viral genomic sequence of HCV is known, as are methods for obtaining the sequence. See, e.g., International Publication Nos. WO 89/04669; WO 90/11089; and WO 90/14436. The HCV genome encodes several viral proteins, including El (also known as E) and E2 (also known as E2/NSI). (See, Houghton et al. *Hepatology* (1991) 14:381–388, for a discussion of HCV proteins, including El and E2.) The sequences encoding each of these proteins, as well as antigenic fragments thereof, will find use in the present methods. Similarly, the coding sequence for the δ-antigen from HDV is known (see, e.g., allowed U.S. patent application Ser. No. 07/912,127) and this sequence can also be conveniently used in the present methods.

Polynucleotide sequences encoding proteins derived from other viruses will also find use in the claimed methods, such as without limitation, proteins from members of the families Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae (e.g., HTLV-I; HTLV-II; HIV-1 (also known as HTLV-III, LAV, ARV, hTLR, etc.), including but not limited to antigens from the isolates $HIV_{IIIb}$, $HIV_{SF2}$, $HIV_{LAV}$, $HIV_{LAP}$, $HIV_{MN}$); HIV-2; simian immundeficiency virus (SIV) among others. See, e.g. Virology, 3rd Edition (W. K. Joklik ed. 1988); *Fundamental Virology*, 2nd Edition (B. N. Fields and D. M. Knipe, eds. 1991), for a description of these and other viruses.

The present invention has been exemplified using the gene encoding the gp120 envelope protein from $HIV_{SF2}$. However, the gp120 sequences for a multitude of additional HIV-1 and HIV-2 isolates, including members of the various genetic subtypes of HIV, are known and reported (see, e.g., Myers et al. Los Alamos Database, Los Alamos National Laboratory, Los Alamos, N.Mex. (1992); Myers et al., Human Retroviruses and Aids, 1990, Los Alamos, N.Mex.: Los Alamos National Laboratory; and Modrow et al. *J. Virol.* (1987) 61:570–578, for a comparison of the envelope gene sequences of a variety of HIV isolates) and sequences derived from any of these isolates will find use in the present methods. Furthermore, the invention is equally applicable to other immunogenic proteins derived from HIV, such as the envelope proteins gp41 and gp160, as well as gag and pol.

As explained above, influenza virus is another example of a virus for which the present invention will be particularly useful. Specifically, the envelope glycoproteins HA and NA of influenza A are of particular interest for generating an immune response. Numerous HA subtypes of influenza A have been identified (Kawaoka et al. *Virology* (1990) 179:759–767; Webster et al. "Antigenic variation among type A influenza viruses," p. 127–168. In: P. Palese and D. W. Kingsbury (ed.), *Genetics of influenza viruses*. Springer-Verlag, New York). Thus, the gene sequences encoding proteins derived from any of these isolates can also be used in the nucleic acid immunization techniques described herein.

Furthermore, the method described herein provides a means for treating a variety of malignant cancers. For example, the infection/transfection system of the present invention can be used to mount a cell-mediated immune response to particular proteins specific to the cancer in question, such as an activated oncogene, a fetal antigen, or an activation marker. Such tumor antigens include any of the various MAGEs (melanoma associated antigen E), including MAGE 1, 2, 3, 4, etc. (Boon, T. *Scientific American* (March 1993):82–89); any of the various tyrosinases; MART 1 (melanoma antigen recognized by T cells), mutant ras; mutant p53; p97 melanoma antigen; CEA (carcinoembryonic antigen), among others.

It is readily apparent that the subject invention can be used to prevent or treat a wide variety of viral diseases.

The present invention can also be used to transiently and locally express immune modulating agents which can enhance antigen presentation, attract lymphocytes to the site of gene expression or promote expansion of the population of lymphocytes to the site of gene expression or promote expansion of the population of lymphocytes which respond to the expressed antigen. Such molecules include cytokines, lymphokines, and chemokines, including but not limited to IL-2, modified IL-2 (cys125·:ser125), GM-CSF, IL-12, γ-interferon, IP-10, MIP1β and RANTES. Additionally, immune molecules such as TAP transporters, B7, β2M, class I or II MHC genes (syngeneic or allogeneic) and other genes coding for proteins that are required for efficient immune responses but are not expressed due to specific inhibition or deletion, will also find use for expression using the present invention. This is particularly relevant in tumor cells and in some infected cells where antigen presentation is often reduced.

The present system is also useful for the expression of proteins in different cellular compartments that might influence antigen presentation. For example, a protein that is normally secreted (with a signal sequence) or is nuclear-bound can be engineered to be retained at the cell surface or in the endoplasmic reticulum with the addition of the appropriate anchor sequence. Such relocalization may lead to more efficient class I- or class II- restricted antigen presentation as these proteins may be more accessible for those processes that lead to degradation of proteins into peptides for subsequent association with the appropriate MHC molecule.

Polynucleotide sequences coding for the above-described molecules can be obtained using recombinant methods, such as by screening cDNA and genomic libraries from cells expressing the gene, or by deriving the gene from a vector known to include the same. Furthermore, the desired gene can be isolated directly from cells and tissues containing the same, using standard techniques, such as phenol extraction and PCR of cDNA or genomic DNA. See, e.g., Sambrook et al., supra, for a description of techniques used to obtain and isolate DNA. The gene of interest can also be produced synthetically, rather than cloned. The nucleotide sequence can be designed with the appropriate codons for the particular amino acid sequence desired. In general, one will select preferred codons for the intended host in which the sequence will be expressed. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

Next, the gene sequence encoding the protein in question is inserted into a vector which includes control sequences operably linked to the desired coding sequence, using methods known to those of skill in the art. In particular, the vector will include at least the bacteriophage T7 promoter which will direct the expression of the antigen coding sequence in the presence of bacteriophage T7 RNA polymerase. The T7 promoter and vectors containing the same are readily available from e.g., Sigma, Boehninger Mannheim, Promega, etc. Transcription termination and polyadenylation sequences may also be present, located 3' to the translation stop codon.

5'- UTR sequences can also be placed adjacent to the coding sequence in order to enhance expression of the antigen in question. Particularly useful for enhancing expression of sequences under the control of the T7 promoter are UTRs which include an Internal Ribosome Entry Site (IRES) present in the leader sequences of picornaviruses such as the encephalomyocarditis virus (EMCV) UTR (Jang et al. *J. Virol.* (1989) 63:1651–1660. Other picornavirus UTR sequences that will also find use in the present invention include the polio leader sequence and hepatitis A virus leader.

Furthermore, plasmids can be constructed which include a chimeric gene sequence, encoding e.g., a viral or tumor antigen and an immune modulating agent as described above. The modulator gene sequence can either precede or follow the gene encoding the protein of interest in a dicistronic gene configuration. An additional IRES leader can be situated between the two genes for efficient translation of RNA from the distal coding region. Alternatively, a chimeric transcription unit having a single open reading frame encoding both the gene of interest and the modulator, can also be constructed. Either a fusion can be made to allow for the synthesis of a chimeric protein or alternatively, protein processing signals can be engineered to provide cleavage by a protease such as a signal peptidase, thus allowing liberation of the two or more proteins derived from translation of the template RNA. Such signals for processing of a polyprotein exist in flaviviruses, pestiviruses such as HCV, and picornaviruses, and can be engineered into the T7-based expression template(s). The processing protease, such as HCV NS3, may also be expressed in this system either independently or as part of a chimera with the antigen and/or cytokine coding region(s). The protease itself can be both a processing enzyme and a vaccine antigen.

Once the construction of the vectors bearing the gene of interest is complete, it may be desirable to encapsulate the vector in lipids prior to delivery to the vertebrate subject or to cells derived therefrom. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, *Biochim. Biophys. Acta.* (1991) 1097:1–17; Straubinger et al., in *Methods of Enzymology* (1983), Vol. 101, pp. 512–527.

Liposomal preparations for use in the instant invention include cationic (positively charged), anionic (negatively charged) and neutral preparations, with cationic liposomes particularly preferred. Cationic liposomes have been shown to mediate intracellular delivery of plasmid DNA (Felgner, et al. *Proc. Natl. Acad. Sci. USA* (1987) 84:7413–7416); mRNA (Malone, et al. *Proc. Natl. Acad. Sci. USA* (1989) 86:6077–6081); and purified transcription factors (Debs, et al. *J. Biol. Chem.* (1990) 265:10189–10192), in functional form.

Cationic liposomes are readily available. For example, N[1-2,3-dioleyloxy)propyl]-N,N,N-triethyl-ammonium (DOTMA) liposomes are available under the trademark Lipofectin, from GIBCO BRL, Grand Island, N.Y. (See, also, Felgner, et al. *Proc. Natl. Acad. Sci. USA* (1987) 84:7413–7416). Other commercially available liposomes include transfectace (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* (1978) 75:4194–4198; PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilamellar vesicles (MLVs), small unilamellar vesicles (SUVs), or large unilamellar vesicles (LUVs). The various liposome-nucleic acid complexes are prepared using methods known in the art. See, e.g., Straubinger et al. in *Methods of Immunology* (1983), Vol. 101, pp. 512–527; Szoka et al. *Proc. Natl. Acad. Sci. USA* (1978) 75:4194–4198; Papahadjopoulos et al. *Biochim. Biophys. Acta* (1975) 394:483; Wilson et al. *Cell* (1979) 17:77); Deamer, D. and Bangham, A. *Biochim. Biophys. Acta* (1976) 443:629; Ostro et al. *Biochem. Biophys. Res. Commun.* (1977) 76:836; Fraley et al. *Proc. Natl. Acad. Sci. USA* (1979) 76:3348); Enoch, H. and Strittmatter, P. *Proc. Natl. Acad. Sci. USA* (1979) 76:145); Fraley, et al. *J. Biol. Chem.* (1980) 255:10431; Szoka, F. and Papahadjopoulos, D. *Proc. Natl. Acad. Sci. USA* (1978) 75:145; and Schaefer-Ridder, et al. *Science* (1982) 215:166.

The vector, either with or without associated lipids, is then formulated into a vaccine composition, as described more fully below, for delivery to the vertebrate subject or to cells obtained therefrom. As explained above, the presence of T7 RNA polymerase will serve to drive the expression of the coding sequence present in the above-described vectors. Accordingly, T7 RNA polymerase is provided either prior, subsequent or concurrent with administration of the nucleic acid sequence of interest, using any of several methods. For example, T7 RNA polymerase protein can be administered directly with the nucleic acid sequence of interest. T7 RNA polymerase is commercially available from e.g., Boehninger Mannheim and Promega. Alternatively, recombinant vectors can be constructed which include the gene encoding T7 RNA polymerase and these vectors can be administered directly to the vertebrate subject, or to a cell extracted therefrom. The T7 RNA polymerase gene can be derived from nucleic acid which encodes the T7 bacteriophage, readily available from, e.g., Sigma (St. Louis, Mo.). The vector is constructed such that the T7 polymerase gene is under the control of regulatory elements which serve to direct transcription and translation of the gene in vivo. If expression is desired using the host's enzymes (such as by the use of endogenous RNA polymerase), the T7 RNA polymerase gene will be operatively linked to regulatory sequences recognized by the particular host, or even particular cells within the host. Thus, eucaryotic and phage regulatory elements will generally be present for expression in mammalian hosts. Such regulatory sequences are known in the art and include but are not limited to promoters derived from SV40, CMV, HSV, RSV, MMTV, T7, T3, among others. Other regulatory sequences, such as transcription termination and polyadenylation sequences, as well as enhancer elements, can also be used in the constructs to increase expression level, as described above. The construction of recombinant vectors containing the T7 RNA polymerase gene is known. See, e.g., Elroy-Stein and Moss, *Proc. Natl. Acad. Sci. USA* (1990) 87:6743–6747, for a description of the construction of the vector pOSV-T7RP, which includes the 10 T7 RNA polymerase gene.

A particularly preferred system for introducing T7 RNA polymerase to the vertebrate subject or cells derived therefrom involves the use of viral vectors such as those derived from the pox family of viruses, including vaccinia virus and avian poxvirus, as well as retroviral and adenoviral vectors. The use of these vectors to deliver gene sequences is well known in the art.

For example, methods for the insertion and expression of foreign genes in vaccinia virus have been described in detail. See, e.g., Mackett, M. et al. in *DNA Cloning: A Practical Approach*, vol. II (D. Glover, ed.) pp. 191–211; Mackett et al. *J. Virol.* (1984) 49:857–864. Briefly, the methods comprise introducing the T7 RNA polymerase gene into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the T7 RNA polymerase into the viral genome. The resulting TK⁻ recombinant can be selected by culturing the cells in the presence of 5-bromodeoxyuridine and picking viral plaques resistant thereto. See, e.g., Fuerst et al. *Proc. Natl. Acad. Sci. USA* (1986) 83:8122–8126, for a description of the construction of a recombinant vaccinia virus including the T7 RNA polymerase gene.

Alternatively, Avipoxviruses, such as the fowlpox and canarypox viruses, can also be used to deliver the T7 RNA polymerase gene. Recombinant avipox viruses, expressing immunogens from mammalian pathogens, are known to confer protective immunity when administered to non-avian species. The use of an Avipox vector is particularly desirable in human and other mammalian species since members of the Avipox genus can only productively replicate in susceptible avian species and therefore are not infective in mammalian cells. Methods for producing recombinant Avipox-viruses are known in the art and employ genetic recombination, as described above with respect to the production of vaccinia viruses. See, e.g., WO 91/12882; WO 89/03429; and WO 92/03545.

Similarly, the delivery of genes using retroviral and adenoviral systems is known and will find use for delivering T7 RNA polymerase to a host. See, e.g., U.S. Pat. No. 5,219,740; International Publication Nos. WO 90/01870 (published Mar. 8, 1990), WO 93/04167 (published Mar. 4, 1993) and WO 93/17118 (published Sep. 2, 1993), for a description of the construction of retroviral vectors and U.S. Pat. No. 5,173,414; International Publication Nos. WO 92/01070 (published Jan. 23, 1992) and WO 93/03769 (published Mar. 4, 1993); Carter, B. J. (1992) *Current Opinion in Biotechnology* 3:533–539; and Muzyczka, N. (1992) *Current Topics in Microbiol. and Immunol.* 158:97–129, for a description of the construction of adenoviral systems for gene delivery.

Molecular conjugate vectors, such as the adenovirus chimeric vectors described in Michael et al. *J. Biol. Chem.* (1993) 268:6866–6869 and Wagner et al. *Proc. Natl. Acad. Sci. USA* (1992) 89:6099–6103, can also be used for gene delivery.

As an alternative approach to infection with Vaccinia or Avipox virus recombinants, or to the delivery of genes using other viral vectors, an amplification system can be used that will lead to high level expression following introduction into host cells.

Specifically, a T7 RNA polymerase promoter preceding the coding region for T7 RNA polymerase can be engineered. Translation of RNA derived from this template will generate T7 RNA polymerase which in turn will transcribe more template. Concomitantly, there will be a cDNA whose expression is under the control of the T7 promoter.

Thus, some of the T7 RNA polymerase generated from translation of the amplification template RNA will lead to transcription of the desired gene. Because some T7 RNA polymerase is required to initiate the amplification, T7 RNA polymerase can be introduced into cells along with the templatets) to prime the transcription reaction.

The amplification template can be generated by PCR techniques. However the use of a plasmid is preferred. Since high level expression of T7 RNA polymerase appears to be lethal to host cells, the plasmid should be one where expression of T7 RNA polymerase can be controlled. For example, a lac operator can be engineered distal or proximal (or both) to the T7 promoter. The binding of the preexisting lac repressor in the appropriate bacterial strain would interfere with the transcription of the template by blocking access to the promoter by T7 RNA polymerase.

Alternatively, or in combination with the above, a plasmid can be constructed where transcription from a bacterial promoter begins 3' of the T7 gene and continues through the 5' end of the T7 promoter. Such transcription will generate an antisense transcript and reduce or eliminate translation of T7 RNA polymerase RNAS. The second transcription unit consisting of the T7 promoter preceding the gene of interest can be provided by a separate plasmid or can be engineered onto the amplification plasmid. Colocalization of the two transcription units is beneficial for ease of manufacturing and ensures that both transcription unit; will always be together in the cells into which the plasmid is introduced. The T7 RNA polymerase plasmids may include the IRES leader sequences of picornaviruses, as described above. As with the plasmids including the antigen coding sequence, the T7 PNAP plasmids may be encapsulated in lipids prior to formulation in vaccine compositions.

Once complete, the construct bearing the gene of interest and the vector including the T7 RNA polymerase gene can be used individually or in combination, in vaccine compositions. These vaccines may either be prophylactic (to prevent infection) or therapeutic (to treat disease after infection). Additionally, the vaccines can comprise mixtures of one or more antigens, such as glycoproteins derived from more than one viral isolate. Furthermore, to enhance persistence of expression via transcription of the gene of interest in the nucleus of the transfected cell, a recombinant DNA construct(s) containing a strong eukaryotic promoter driving the gene of interest can be introduced concomitantly or subsequently. Additional modulating sequences including enhancers, poly adenylation sites or splicing signals may also be included. The vaccine may also be administered in conjunction with other immunoregulatory agents, for example, immunoglobulins, cytokines, lymphokines, and chemokines, including but not limited to IL-2, modified IL-2 (cys125→ser125), GM-CSF, IL-12, γ-interferon, IP-10, MIPβ and RANTES.

The vaccines will generally include one or more "pharmaceutically acceptable excipients or vehicles" such as water, saline, glycerol, ethanol, etc. Additionally, auxiliary substances, such as wetting or emulsifying agents, pH buffering substances, and the like, may be present in such vehicles.

A carrier is optionally present which is a molecule that does not itself induce the production of antibodies harmful to the individual receiving the composition. Suitable carriers are typically large, slowly metabolized macromolecules such as proteins, polysaccharides, polylactic acids, polyglycollic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen may be conjugated to a bacterial toxoid, such as toxoid from diphtheria, tetanus, cholera, etc.

Adjuvants may also be used to enhance the effectiveness of the vaccines. Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, MT) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox); (3) saponin adjuvants, such as Stimulon (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; and (6) other substances that act as immunostimulating agents to enhance the effectiveness of the composition. Alum and MF59 are preferred.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetylmuramyl-L-alanyl-D-isogluatminyl-L-alanine-2-(1'-2'-dipalmitoyl-sn-glycero-3-huydroxyphosphoryloxy)-ethylamine (MTP-PE), etc.

Typically, the vaccine compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above.

The vaccines will comprise a therapeutically effective amount of the antigen-producing genes, as well as the T7 RNA polymerase or a gene coding therefor and any other of the above-mentioned components, as needed. By "therapeutically effective amount" is meant an amount of nucleic acid which will produce an antigen in sufficient amounts to induce an immunological response (as defined above) in the individual to which it is administered. Preferably, the effective amount is sufficient to bring about treatment, also as defined above. The exact amount necessary will vary depending on the subject being treated; the age and general condition of the individual to be treated; the capacity of the individual's immune system to synthesize antibodies; the degree of protection desired; the severity of the condition being treated; the particular antigen selected and its mode of administration, among other factors. An appropriate effective amount can be readily determined by one of skill in the art. A "therapeutically effective amount" will fall in a relatively broad range that can be determined through routine trials. For example, for purposes of the present invention, an effective dose will be from about 0.05 μg/kg to about 50 mg/kg of the DNA constructs.

Once formulated, the vaccines can be administered directly to the vertebrate subject or, alternatively, delivered ex vivo, to cells derived from the subject. Methods for the ex vivo delivery and reimplantation of transformed cells into a subject are known in the art and described in e.g., International Publication No. WO 93/14778 (published Aug. 5, 1993). Generally, such methods will include dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

Direct delivery of the constructs into the vertebrate subject will generally be accomplished by injection using either a conventional syringe or a vaccine gun. The constructs can be injected either subcutaneously, intraperitoneally or intramuscularly. Other modes of administration include oral and pulmonary administration, suppositories, and transdermal applications. Dosage treatment may be a single dose schedule or a multiple dose schedule.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Materials and Methods

Synthetic Peptides

Peptides representing CTL epitopes in HCV or HIV proteins were synthesized by Chiron Mimotopes (Clayton, Australia) or Research Genetics (Huntsville, Ala.) using fmoc methods. All peptides had free amino and carboxy termini.

Cell Lines

Primary fibroblast cell lines were generated from skin punch biopsies from baboons and chimpanzees. Briefly, 5 mm$^2$ pieces of biopsy tissue were cultured in 25 cm$^2$ tissue culture flasks in Dulbecco's minimum essential (DME) medium containing 20% heat inactivated fetal calf serum (FCS) for 7–10 days. Fibroblasts growing from the explanted tissue were sub-cultured as previously described (Perot et al. *J. Gen. Virol.* (1992) 73:3281–3284) and used as target cells in CTL assays.

Primate CTL Lines

Hepatitis C virus (HCV)-specific CTL lines 503/10D and 503/11.3 that were generated from the liver of chronically infected chimpanzees have been described elsewhere (Erickson et al. *J. Immunol.* (1993) 151:4189–4199. Briefly, both cell lines are CD8+ and recognize HCV antigens in the context of class I MHC molecules. Cell line 503/10D recognizes an epitope (amino acids 1445-TGDFDSVIDC-1454) (SEQ ID NO: 1) in the NS3 protein of HCV, whereas cell line 503/11.3 recognizes an epitope in the E2 HCV protein that spans amino acids 589 to 596 (HPDATYSR) (SEQ ID NO: 2). A baboon immunized with recombinant HIV-1$_{SF2}$ gp120 was the source of CD8+ cell line 56 that recognizes a CTL epitope between amino acids 40 and 49 (GVPVWKEATT) (SEQ ID NO: 3) of the envelope protein.

Murine CTL Cultures

Murine MC57 (H-2$^b$) and SVBalb (H-2$^d$) cell lines have been described elsewhere (Walker et al. *Proc. Natl. Acad. Sci. USA* (1992) 89:7915–7918) and were used as target cells to assay CTL activity from immunized mice.

Recombinant DNA Clones

The following recombinant DNA clones have been previously described in Selby et al. *J. Gen. Virol.* (1993) 74:1103–1113: pEMCV-HCV, pEMCV-CE2, pEMCV-NS25 and pEMCV-NS5. These clones express the full-length open reading frame (ORF) of the HCV genome which encodes the structural and non-structural proteins of HCV (pEMCV-HCV); the structural coding region which encodes the nucleocapsid protein C and the E1 and E2 envelope glycoproteins of HCV (pEMCV-CE2); the non-structural coding region, which encodes the non-structural proteins of HCV including NS2, NS3, NS4a, NS4b, NS5a and NS5b (pEMCV-NS25); and a portion of the non-structural coding region of the HCV genome which encodes much of NS4A and NS4B (pEMCV-NS4); as well as NS5a and NS5b (pEMCV-NS5). (See, FIG. 1). The coding sequences in these clones are under the control of the T7 promoter. These vectors were constructed as follows.

To generate the C9000 clone, several cDNAs isolated from a cDNA library made from infectious chimpanzee plasma 910 (Choo et al. *Science* (1989) 244:359–362) were ligated together such that the nucleotides 68 to 9327 of HCV were present. A new vector, pMS100, was derived to facilitate cloning of the complete HCV genome: the pUC18 polylinker was removed and replaced with synthetic oligonucleotides that included HindIII, NcoI, Asp718, EcoRI, NotI and XbaI restriction sites. Clone p5'#1 was generated by ligating 6 overlapping oligonucleotides specifying a MluI site, a T7 promoter and the first 83 nucleotides of the HCV 5'UTR into the HindIII/NcoI sites of pMS100. A 497 base pair (bp) NcoI/Asp718 fragment from the ssag30a cDNA was cloned into NcoI/Asp718 sites of p5'#1 to generate p5'+. Next, a 8706 bp Asp700/NotI fragment from the C9000 CDNA clone (nucleotides 45 to 9060) was cloned into Asp700(partial)/NotI sites of p5'+ to create pHCV5-1. pHCV5-1 was digested with NotI/XbaI and used as a vector in a ligation with 6 overlapping oligonucleotides that corresponded to the remainder of the HCV cDNA. These oligonucleotides included the NotI site, the remainder of the HCV cDNA, a 15 nucleotide polyA tail and finally a unique XbaI site. The sequence of the resulting clone, pHCV, was verified by sequencing with the Sequenase kit (US Biochemicals). To generate pEMCV-CE2, NcoI/StuI-digested pTM1 (Elroy-Stein and Moss *Proc. Natl. Accd. Sci. USA* (1990) 87:6743–6747) was ligated with 1) a 240 bp PCR product that included an engineered NcoI site at the initiator methionine to the Asp718 site and 2) a 2477 bp fragment from pSB (provided by K. Thudium and R. Ralston), representing HCV sequences from nucleotide 580 (Asp718) to 3035 (amino acid 906), followed by a termination codon. An 8937 bp Asp700/Xba fragment from PHCV was cloned into the Asp700/SpeI sites of pEMCV-CE2 to generate pEMCV-HCV. A NcoI site was created by PCR just before amino acid 2510 of NS2 (at or near the amino terminus of NS2). This 321 bp NcoI/Eco47III PCR product was ligated with a 6569 bp Eco47III/XbaI fragment of PHCV and cloned into NcoI/SpeI sites of pTM1. The resulting clone was designated pEMCV-NS25. To generate pEMCV-NS5, a PCR fragment that included an engineered NcoI site just before amino acid 2014 of HCV and continued to NheI at 6948 was ligated with the 2469 bp NheI/XbaI fragment from pHCV and cloned into NcoI/SpeI sites of pTM1. The resulting clone was designated pEMCV-NS5.

Clone pEMCV-E2$_{730}$, including a portion of the structural coding region of the HCV genome, including the coding region for the envelope glycoprotein E2 (see, FIG. 1), under the control of the T7 promoter, was derived from a PCR reaction with primers, followed by digestion with NcoI and BamHI and cloning into NcoI/BamHI-digested pTM1 (Elroy-Stein and Moss, *Proc. Natl. Acad. Sci. USA* (1990) 87:6743–6747). The pGEM-NS3 clone, containing a portion of the non-structural coding region of the HCV genome including the coding region for the HCV protein NS3, under the control of the T7 promoter, was derived from a PCR reaction with primers, followed by digestion with HindIII and BamHI and cloning into HindIII/BamHI-digested pGEM3Z (Promega). The pEMCV-NS4 clone, also containing a portion of the non-structural coding region of the HCV genome under the control of the T7 promoter, was derived from a PCR reaction with primers, followed by digestion with NcoI and BamHI and cloning into NcoI/BamHI-digested pTM1.

Figure 6:
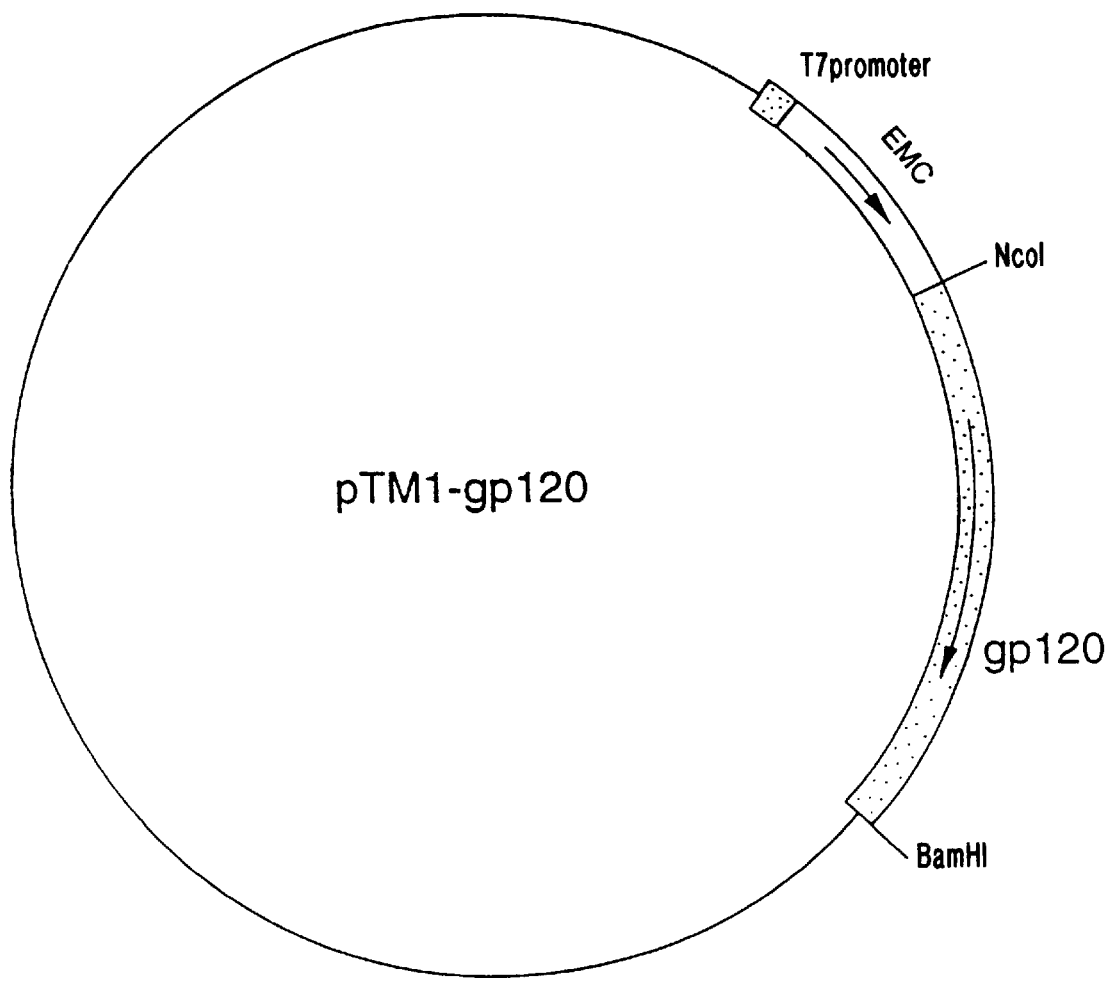
FIG. 6 is a diagram of plasmid pTM1-gp120 (ATCC Accession No. 69638) which includes the HIV gp120 gene under the control of the T7 promoter.

The amino acid coordinates of these clones are indicated in FIG. 1. EMCV signifies a leader sequence derived from endomyocarditis virus which specifies cap-independent initiation of translation. The NS3 coding region in pGEM-NS3 was preceded by a few nucleotides of the remaining pGEM3Z polylinker rather that the EMCV promoter. The A nucleotides at the 3' end of several clones correspond to a polyA tract that consists of 15A residues.

pTM1-gp120 (ATCC Accession No. 69638) was generated by PCR cloning using pCMV6agp120-SF2 (ATCC Accession No. 68249; Chapman et al. Nuc. Acids. Res. (1991) 19:3979–3986) as template and specific 5' and 3' primers so as to amplify the mature gp120 preceded by the tPA leader. This product was digested with NcoI/BamH1 and ligated to NcoI/BamHI-digested pTM1. The resulting construct, pTM1-gp120 (ATCC Accession No. 69638), included the gp120 gene under the control of the T7 promoter (FIG. 6).

pTM1-p55gag was generated by PCR cloning using p9BR7 (York-Higgins et al. *J. Virol.* (1990) 64:4016–4020; Cheng-Mayer et al. *J. Virol.* (1990) 64:4390–4398) as template. Plasmid p9BR7 contains the 5'-half of the HIV SF2 genome, including the gene encoding p55gag. Taq polymerase was used with the 5' (AGGAGAGAGCCATGGGTGCTG) (SEQ ID NO:4) and 3' (CGCGGATCCTATTGTGACGAGGGGTCGTT) (SEQ ID NO:4) primers. The PCR product was purified on a Promega Wizard PRC Prep column and digested with NcoI and BamHI, then ligated into the NcoI/BamHI digested pTM1 vector to yield pTM1-p55gag.

EXAMPLE 1

Expression of HCV Viral Proteins Using Infection/Transfection

To demonstrate the expression of HCV proteins in primary cells after infection/transfection, a chimpanzee fibroblast cell line, designated F503, was infected with VV-T7, a vaccinia virus which expresses the T7 RNA polymerase gene (Elroy-Stein and Moss, *Proc. Natl. Acad. Sci. USA* (1990) 87:6743–6747), and transfected with the pEMCV-CE2, pEMCV-NS25, pEMCV-NS4 or pEMCV-NS5 DNA templates as follows. Monolayers of chimpanzee fibroblast cultures that were approximately 70% confluent in 60 mm tissue culture dishes were washed twice with serum-free DME (SF-DME) and infected with VV-T7 at a multiplicity of infection (m.o.i.) of 10, unless otherwise indicated. At one hour post-infection, the inocula were removed, the monolayers were rinsed once with SF-DME and then transfected with Lipofectin/DNA mixtures, made by diluting the DNA clones pEMCV-CE2, pEMCV-NS25, pEMCV-NS4 and pEMCV-NS5, to 1.5 $\mu$g in a final volume of 50 $\mu$l and mixing with 50 $\mu$l of diluted Lipofectin (Bethesda Research Labs, Rockville, Md.) (30 $\mu$l Lipofectin +20 $\mu$l water per transfection) in polystyrene tubes. After 15 minutes at room temperature, 500 $\mu$l of SF-DME was added to each sample and 600 $\mu$l was gently pipetted onto the monolayers. After a 15 minute incubation at room temperature, an additional 500 $\mu$l of SF-DME was added and the cells were incubated 3–4 hours at 37° C. in 5% $Co_2$.

Cells were labeled by removing the media and replacing it with 1 ml of methionine/cysteine-deficient DME for 30 minutes, followed by the addition of 100 mCi of $^{35}$S-methionine and $^{35}$S-cysteine (New England Nuclear). The cells were labeled for 4–5 hours at 37° C. The media was discarded and the cells were lysed directly in chilled lysis buffer (100 mM NaCl, 20 mM Tris-HCl pH 7.5, 1 mM EDTA, 0.5% NP40 and 0.5% DOC) containing PMSF (100 $\mu$M), leupeptin (0.5 $\mu$g/ml) and aprotinin (2 $\mu$g/ml). The lysates were transferred to microfuge tubes, vortexed, cleared of debris and stored at –80° C. The lysates were re-cleared by centrifugation before use.

The labeled lysates were immunoprecipitated with monospecific antibodies against HCV proteins (Selby et al. *J. Gen. Virol.* (1993) 74:1103–1113) followed by fractionation on 12.5% polyacrylamide gels and autoradio-graphy as follows. Buffer-equilibrated protein A sepharose (Sigma) was added to microfuge tubes to obtain a bed volume of approximately 25 $\mu$l. Next, 150 $\mu$l of lysis buffer was added to each microfuge tube along with 20 $\mu$l of a 1:200 dilution of anti-E2, anti-NS3 (C33c), anti-NS4 (C100) or anti-NS5 antibodies. The microfuge tubes were rocked at 4° C. for 3 hours and washed 3 times with lysis buffer. Unlabeled control lysates of cells infected with VV-T7 were added to the protein A sepharose-absorbed antibodies to reduce background. After 3 hours, the beads were washed 3 times and incubated overnight with approximately 20% of the labeled lysate at 4° C. Samples were washed 4 times in lysis buffer and 50 $\mu$l of Laemmli sample buffer was added to each tube. The samples were boiled and 25 $\mu$l loaded onto 12.5% polyacrylamide gels for electrophoresis. The gels were fixed in 50% methanol/10% acetic acid, treated with Enhance (New England Nuclear), dried and exposed to film with an intensifying screen.

Results of the experiment are shown in FIG. 2. In particular, FIG. 2A shows the results of the transfections with pEMCV-$\mu$gal, (control DNA expressing $\mu$-galactosidase) (lanes 1 and 3), pEMCV-CE2 (lane 3) or pEMCV-NS25. The labeled lysates were immunoprecipitated with rabbit anti-E2 antibody (lanes 1 and 2) or rabbit anti-NS3 (anti-C33c) (lanes 3 and 4). Envelope glycoprotein E2 (gp68–76 kd) is denoted by a bracket as is E1 (gp32), which is co-immunoprecipitated by E2-specific antibody. NS3 is denoted by an arrow and has a molecular weight of 72 kd. S denotes $^{14}$C-labeled molecular weight standards (Bethesda Research Labs); the molecular weights are shown on the left. FIG. 2B shows the results of the transfections with no DNA or with pEMCV-NS4. The labeled lysates were immunoprecipitated with anti-NS4 (anti-C100) antibody. The migration of NS4 is denoted by an arrow. The NS4 reactive protein expressed from this construct was not processed into NS4a and NS4b because the protease responsible for its cleavage, NS3, was not co-expressed here. FIG. 2C shows the results of transfections with no DNA or pEMCV-NS5. The labeled lysates were immunoprecipitated with anti-NS5 antibody. The migration of NS5 (~120 kd) is denoted by an arrow. The NS5 reactive protein expressed from this construct was not processed into NS5a and NS5b because the NS3 protease responsible for its cleavage was not co-expressed.

As shown in FIG. 2, immunoreactive proteins with electrophoretic mobilities identical to those previously described for HCV E2, E1 and NS3 proteins were observed. The NS4 and NS5 species were larger than those observed in transfections with larger templates because the NS3-encoded protease responsible for bifurcation of these two proteins was not co-expressed in these transfections. However, co-transfection of the NS4 and NS5 templates with NS3-coding templates resulted in trans-processing into the respective A and B proteins. Other faint bands may correspond to co-immunoprecipitated HCV proteins. These results demonstrate that chimpanzee fibroblasts express HCV proteins after infection/transfection.

EXAMPLE 2

Expression of HIV Viral Proteins Using Infection/Transfection.

Figure 3:
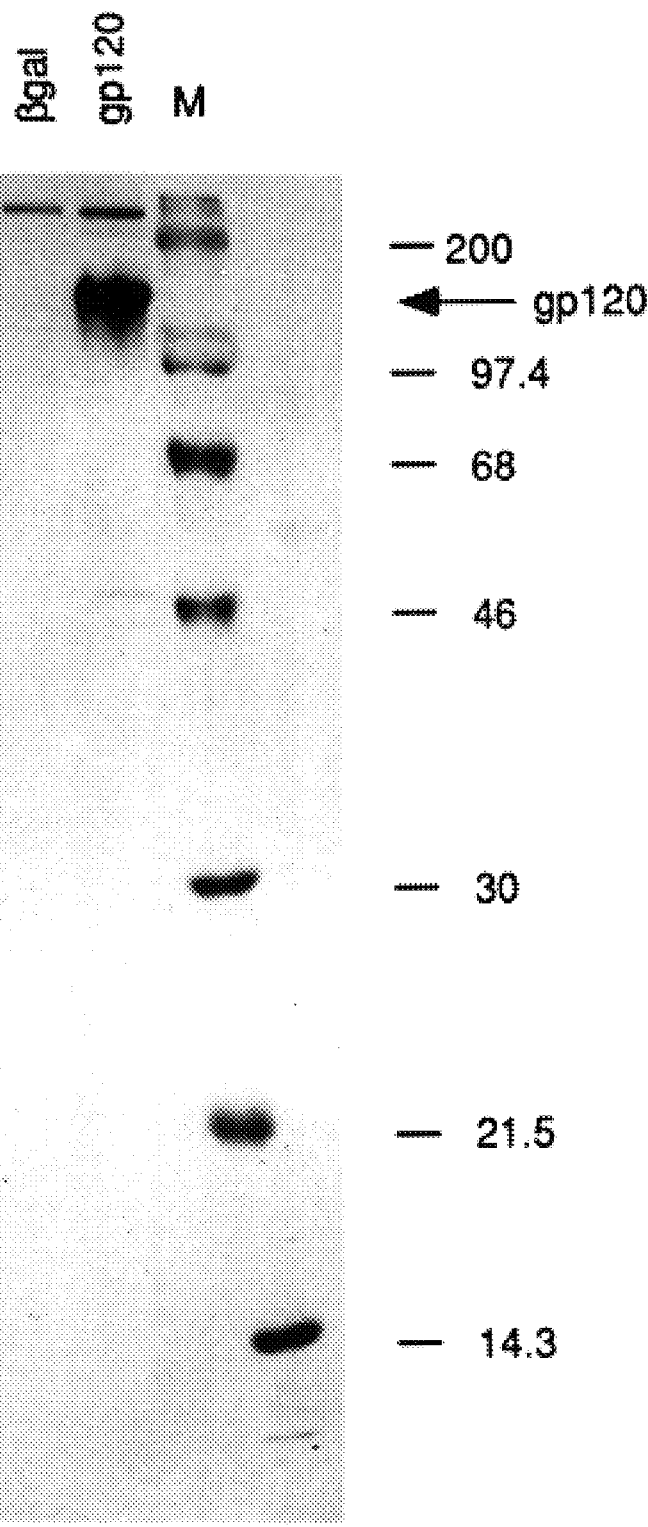
FIG. 3 is a representation of an autoradiograph of a polyacrylamide gel showing the immunprecipitation of chimpanzee fibroblasts transfected with pTM1-gp120 (ATCC Accession No. 69638). Immunoreactive gp120 is denoted by the arrow.

Primary chimpanzee fibroblasts were infected with VV-T7 and transfected with pTM1-gp120 (ATCC Accession No. 69638), encoding the external envelope protein of HIV-1, gp120, as described in Example 1. Cells infected and transfected with pTM1-gp120 (ATCC Accession No. 69638) were immunoprecipitated with HIV positive antisera and fractionated on a 12.5% acrylamide gel as described in Example 1. The results are shown in FIG. 3. Immunoreactive gp120 is denoted by the arrow. As shown in FIG. 3, results similar to those in Example 1 were obtained. A band with the predicted molecular weight of 120 kd was observed when cell lysates were immunoprecipitated with HIV envelope-specific antibodies and analyzed by gel electrophoresis.

EXAMPLE 3

CTL-Mediated Lysis of Primary Fibroblasts Expressing HCV Proteins

To demonstrate that the infection/transfection system described in the preceding examples resulted in cytoplasmic expression, CTL cytotoxic cell assays were conducted as follows. Clonal class I MHC restricted, CD8+ CTL lines, specific for HCV proteins, were generated from the liver of a chronically infected chimpanzee as described in Erickson et al. *J. Immunol.* (1993) 151:4189–4199. Clone 503/11.3 recognizes an epitope between amino acids 592 and 601 (KHPDATYSRC) (SEQ ID NO:6) in the E2 protein of HCV-1. A synthetic peptide, p206B, which represents this sequence, was synthesized as described above. To assay cytotoxic activity, target cells were incubated with 50 $\mu$Ci of $^{51}$Cr for 60 min. Synthetic peptide p206B was added to target cells at a 20 $\mu$M concentration during $^{51}$Cr labelling. After 3 washes, 5×10$^3$ target (T) cells were cultured with CD8+ effector (E) cells at various E:T ratios, as shown in Table 1, in 200 $\mu$l of CM in a 96-well round bottom tissue culture plate for 4 hours. The average cpm from duplicate wells was used to calculate percent specific $^{51}$Cr release as described elsewhere (Erickson et al. *J. Immunol.* (1993) 151:4189–4199).

As shown in Table 1, syngeneic F503 fibroblasts sensitized with the synthetic peptide p206B were killed by cell line 503/11.3, whereas untreated F503 cells were not. Significant levels of cytotoxic activity were not observed against F503 cells that were infected with VV-T7 followed by transfection with DNA encoding the non-structural proteins of HCV (pEMCV-NS25). In contrast, VV-T7-infected cells that were transfected with plasmids encoding E2 (pEMCV-E2$_{730}$), HCV structural proteins (pEMCV-CE2), or the entire HCV polyprotein (pEMCV-HCV) were sensitized for lysis by the E2-specific CTL line. These results indicate that the infection/transfection system resulted in cytoplasmic expression of the antigens and that recognition of the transfected cells by 503/11.3 was antigen-specific.

TABLE 1

| | | Specific Lysis of Target Cells (Percent specific lysis of autologous F503 targets) | | |
|---|---|---|---|---|
| p206.B | DNA | E:T = 50:1 | E:T = 12:1 | E:T = 3:1 |
| − | − | 5 | 4 | 3 |
| + | − | 70 | 49 | 26 |
| − | pEMCV-NS25 | 13 | 12 | 11 |
| − | pEMCV-E2$_{730}$ | 52 | 41 | 28 |
| − | pEMCV-CE2 | 41 | 28 | 13 |
| − | pEMCV-HCV | 30 | 26 | 25 |

EXAMPLE 4

Specificity of CTL-mediated Lysis of Primary Fibroblasts Expressing HCV Proteins To further characterize the specificity of this cytotoxic activity, CTL line 503/10D was tested for the ability to kill the panel of transfected F503 cell lines using the techniques described in Example 3, and p189.2, a synthetic peptide that represents the epitope occurring at amino acid 1445-TGDFDSVIDC-1454 SEQ ID NO:1) in the NS3 protein of HCV. High levels of lysis were observed against F503 cells that were pretreated with p189.2.

TABLE 2

| | | Treatment of Target Cells | | Specific Lysis of Target Cells (E:T ratio) | | |
|---|---|---|---|---|---|---|
| Exp. | Target | p189.2 | DNA | 50:1 | 12:1 | 3:1 |
| 1 | F503 | − | − | 3 | 4 | 3 |
| | | + | − | 54 | 34 | 12 |
| | | − | pGEM-NS3 | 37 | 30 | 15 |
| | | − | pEMCV-NS25 | 47 | 51 | 31 |
| | | − | pEMCV-HCV | 41 | 33 | 20 |
| | | − | pEMCV-CE2 | 1 | 2 | <1 |
| | F635 | − | pEMCV-CE2 | 1 | 8 | 3 |
| | | − | pEMCV-NS25 | 13 | 13 | 4 |
| 2 | F503 | − | − | 4.5 | 2.1 | 4.8 |
| | | + | − | 73 | 46 | 19 |
| | F635 | − | − | 3.1 | 1.3 | 1.8 |
| | | + | − | 2.5 | 3.2 | 2.2 |

Significant levels of lysis were also observed against F503 cells transfected with DNA encoding NS3 (pEMCV-NS25, pEMCV-HCV, and pGEM-NS3), but not those receiving DNA encoding structural proteins (pEMCV-CE2) (Table 2, Experiment 1). Class I MHC restriction of the cytotoxic activity was documented against the histoincompatible F635 fibroblast cell line generated from an unrelated chimpanzee. This cell line was not lysed by 503/10D when sensitized with p189.2, indicating that it does not carry the appropriate class I MHC allele required for presentation of the epitope (Table 2, Experiment 2). Transfection of VV-T7-infected F635 cells with the pEMCV-NS25 plasmid did result in lysis by 503/10D. These data indicate that recognition of the transfected cells by HCV-specific CTL clones was antigen-specific and class I MHC-restricted.

EXAMPLE 5

Optimal Conditions for Infection/Transfection of Chimpanzee Fibroblasts

Figure 4:
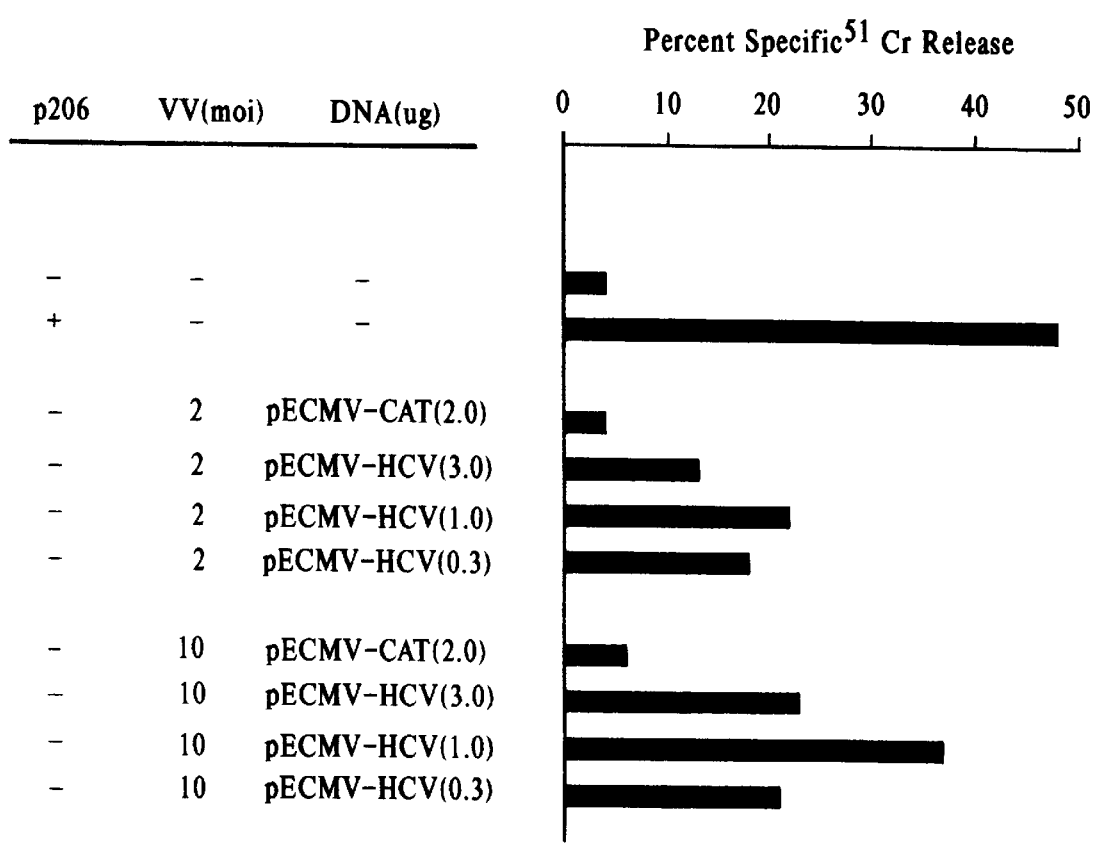
FIG. 4 depicts the percent specific $^{51}$Cr release from F503 target cells infected with the indicated VV-T7 multiplicities of infection (m.o.i.) and transfected with the indicated concentrations of DNA.

VV-T7 and viral DNA were titrated on F503 fibroblasts to establish the optimal conditions for class I MHC presentation of HCV proteins. F503 target cells were sensitized with 10 $\mu$M of p206, or were infected with VV-T7 at an m.o.i. of 2 or 10 before transfection, with the concentration of pECMV-HCV or pECMV-CAT DNA as indicated in FIG. 4. After $^{51}$Cr labelling, targets (T) were co-cultured with 503/11.3 effector (E) cells at an E:T ratio of 50:1 in a 4 h assay. As shown in FIG. 4, VV-T7-infected cells that were transfected with a control plasmid expressing chloramphenicol acetyl transferase (pEMCV-CAT) were not killed. Comparison of target cells infected with VV-T7 at an m.o.i. of 10 or 2 revealed that the higher virus input resulted in consistently higher levels of HCV-specific lysis. An input of 1 $\mu$g of DNA was optimal for sensitization of target cells.

EXAMPLE 6 gp120-Specific Lysis of Baboon Fibroblasts by a CD8+ CTL Line

Figure 5:
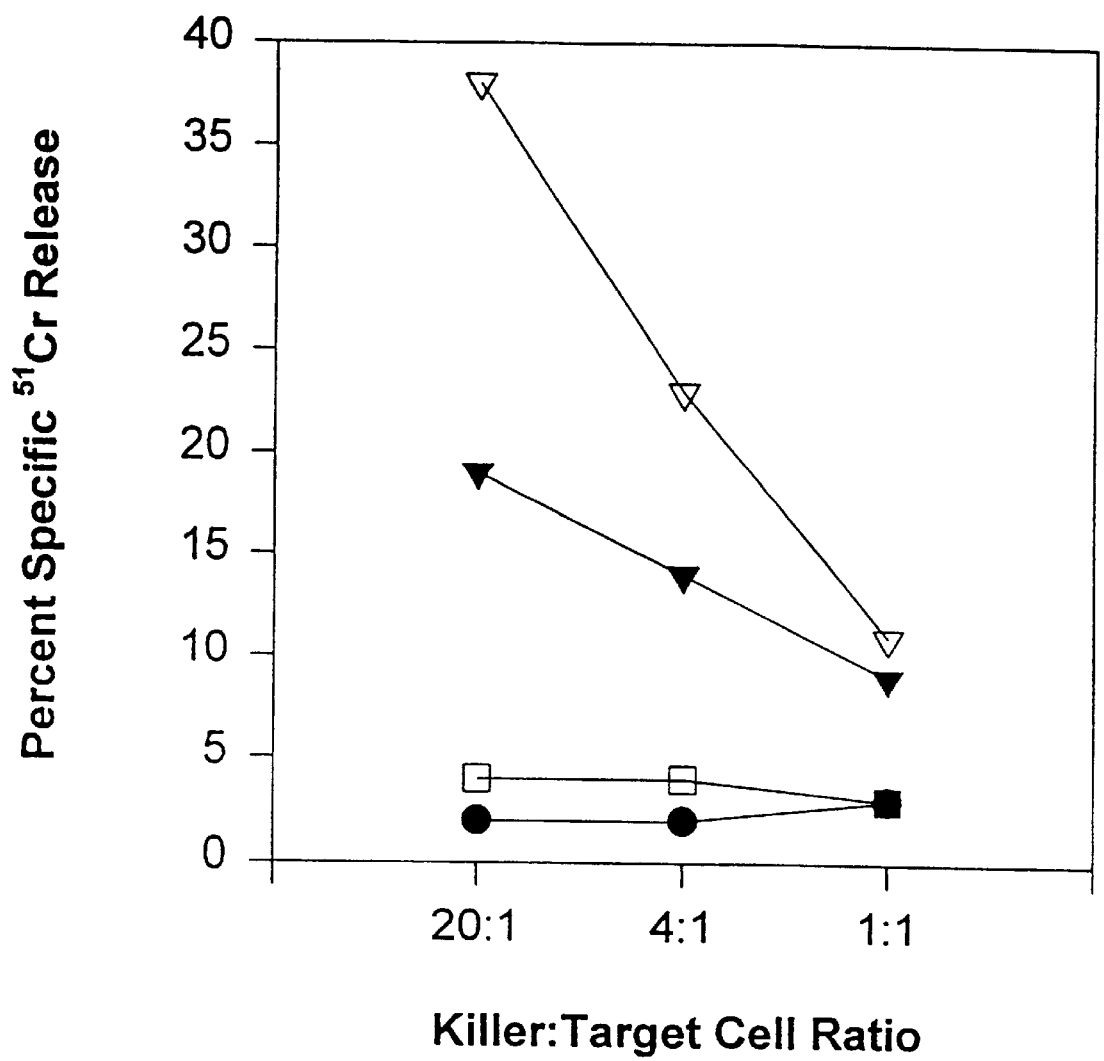
FIG. 5 depicts the percent specific $^{51}$Cr release from VV-T7-infected target cells which were untreated (●), incubated with the epitopic peptide (inverted triangle), transfected with pTM1-gp120(ATCC Accession No. 69638) DNA (solid inverted triangle) or transfected with pEMCV-βgal (□), and incubated with gp120-specific CD8+ cell line.

To determine whether DNA encoding other viral proteins could sensitize target cells for CTL lysis, VV-T7-infected (at an m.o.i of 10) primary baboon fibroblasts were transfected with pTM1-gp120 (ATCC Accession No. 69638) DNA and tested for lysis by an autologous CD8+ CTL line specific for the HIV envelope protein, using the methods described in Example 1. After labelling with $^{51}$Cr, target cells were (a) untreated, (b) incubated with the epitopic peptide, (c) transfected with pTM1-gp120 (ATCC Accession No. 69638), or (d) transfected with control DNA expressing βgal. These cells were then incubated with a gp120-specific CD8+ cell line at an E:T ratio of 20:1 in a 4 hr assay. FIG. 5 shows that levels of killing against the pTM1-gp120-transfected target cell were approximately 50 percent of those observed against a peptide-sensitized target, but were significantly greater than those observed with cells receiving a control DNA plasmid.

EXAMPLE 7

Priming of CTL Responses in vivo by Infection/Transfection

A. The ability of DNA under the control of the T7 promoter to elicit class I MHC restricted CTL in an animal model was assessed as follows. Balb/c (H-2$^d$) mice were purchased from Charles River Laboratories and used between 5 and 12 weeks of age. Mice were infected intraperitoneally with 1×10$^7$ plaque forming units (pfu) of VV-T7 or VV-gp160, a recombinant vaccinia virus expressing the HIV-1 envelope protein, gp160. Animals receiving the VV-T7 vector also received i.p. injections of DOTAP (1,2-bis(oleyloxy)-3-(trimethylammonio)propane) (Boehringer Mannheim)-encapsulated pTM1-gp120 (ATCC Accession No. 69638) DNA at 1 and 18 hours post-infection. Three weeks later splenic T cells from these animals were restimulated in vitro with a synthetic peptide representing a CTL epitope in the V3 portion of the molecule. Spleen cells from immunized mice were cultured in 24 well plates at 4×10$^6$ cells per well in 1 ml of culture medium (CM) consisting of RPMI 1640 supplemented with 10% FCS and 5% IL 2 (Rat T Stim; Collaborative Research Products, Bedford, Mass.). A synthetic peptide representing a CTL epitope within the V3 domain of gp120 was added to CM at a 10 μM concentration. After five days of incubation at 37° C. in a humidified incubator, cells were washed once and readjusted to a concentration of 2×10$^6$ per ml of CM. Cells were tested for CTL activity 2 days later as described in Example 3. Killing was assessed after five days of culture against histocompatible and incompatible target cells sensitized with the V3 loop peptide. As shown in Table 3, high levels of lysis were observed when class I MHC matched target cells sensitized with the V3 peptide were incubated with effector cells from the VV-gp160 infected mice. Significantly, V3-loop specific CTL were also detected in cultures of spleen cells from the mice receiving VV-T7 and gp120 DNA. Levels of lysis were approximately 30–40 percent of those observed with effector cells from the VV-gp160 infected animals. The data clearly indicate that the infection/transfection technique elicits virus-specific, class I MHC restricted CTL responses in vivo.

TABLE 3

| | | | Percent Specific Lysis of Target Cells | | | |
| | | | | SVBalb | | MC57 |
|---|---|---|---|---|---|---|
| VV Vector | DNA Route | E:T Ratio | Untreated | pV3 (SF2) | pV3 (IIIb) | pV3 (SF2) |
| VVgp160 | none | 50:1 | 3 | 81 | 1 | 1 |
| | | 10:1 | <1 | 63 | <1 | 2 |
| | | 2:1 | 2 | 32 | <1 | 1 |

TABLE 3-continued

| | | | Percent Specific Lysis of Target Cells | | | |
| | | | | SVBalb | | MC57 |
|---|---|---|---|---|---|---|
| VV Vector | DNA Route | E:T Ratio | Untreated | pV3 (SF2) | pV3 (IIIb) | pV3 (SF2) |
| VVT7 | i.p. | 50:1 | 2 | 29 | <1 | <1 |
| | | 10:1 | 4 | 12 | <1 | <1 |
| | | 2:1 | 2 | 8 | <1 | 2 |
| VVT7 | i.v. | 50:1 | 5 | 37 | 3 | 1 |
| | | 10:1 | 5 | 17 | 2 | 1 |
| | | 2:1 | 3 | 7 | 2 | 2 |

B. A second experiment was done to determine whether DNA plasmids encoding foreign antigens under the control of the T7 polymerase promoter would elicit class I MHC restricted CTL responses in an animal model. Balb/c mice were infected via the intraperitoneal (i.p.) route with 1×10$^7$ pfu of VV-T7, as described above. Two hours later, 25 μg of pTM1-gp120 encoding the HIV-1 gp120 (Table 4) or pTM1-p55gag, encoding the HIV p55gag protein (Table 5), each under the control of the T7 polymerase promoter, were injected i.p. in the presence or absence of 155 μg of the cationic lipid DOTAP. Injections with the DNA plasmids were repeated 18 hours later.

Four weeks later spleen cell suspensions from these animals were restimulated in vitro with peptides representing gp12o (pV3) or p55gag (p7) CTL epitopes. CTL activity was assessed 7 days later against $^{51}$Cr-labelled histocompatible (SVBalb) and histoincompatible (MC57) target cells pulsed with the epitopic peptides.

As can be seen in Tables 4 and 5, DNA plasmids containing the HIV-1 gp120 (Table 4) or p55gag (Table 5) genes under the control of the T7 promoter elicited class I MHC restricted CTL activity in mice when T7 protein was delivered through infection with VV-T7. Effector cells from mice immunized with the gp120 plasmid killed MHC-matched (i.e. SVBalb) target cells that were treated with the relevant epitopic peptide (pV3) but not those that were untreated or treated with an irrelevant peptide (i.e. p41). Similar results were obtained with spleen cells from mice immunized with p55gag plasmid.

Co-administration of the plasmids and a wild-type vaccinia virus (VVwt) that did not express T7 protein was not sufficient to cause priming of the CTL response. DOTAP was required for efficient immunization with the DNA plasmids in these experiments.

TABLE 4 gp120-specific CTL in Mice Immunized with gp120 DNA and VV-T7

| | | | | Percent Specific Lysis of Targets: | | | |
| | | | E:T | | SVBalb | | MC57 |
|---|---|---|---|---|---|---|---|
| Vaccinia | DNA | DOTAP | Ratio | None | p41 | pV3 | pV3 |
| VVT7 | gp120 | + | 40:1 | 15 | 12 | 58 | 9 |
| | | | 10:1 | 10 | 9 | 28 | 7 |
| | | | 2:1 | 6 | 5 | 11 | 3 |
| VVT7 | gp120 | − | 40:1 | 14 | 13 | 18 | 4 |
| | | | 10:1 | 9 | 7 | 6 | 2 |
| | | | 2:1 | 5 | 2 | 5 | 2 |

TABLE 4-continued gp120-specific CTL in Mice Immunized with gp120 DNA and VV-T7

| | | | | Percent Specific Lysis of Targets: | | | |
|---|---|---|---|---|---|---|---|
| | | | E:T | | SVBalb | | MC57 |
| Vaccinia | DNA | DOTAP | Ratio | None | p41 | pV3 | pV3 |
| VVwt | gp120 | + | 40:1 | 14 | 9 | 8 | 1 |
| | | | 10:1 | 9 | 5 | 6 | 4 |
| | | | 2:1 | 7 | 3 | 6 | 2 |
| VVgp160 | — | – | 40:1 | 12 | 9 | 92 | 10 |
| | | | 10:1 | 9 | 6 | 74 | 2 |
| | | | 2:1 | 1 | 1 | 29 | 1 |

TABLE 5 p55gag-specific CTL in Mice Immunized with p55gag DNA and VV-T7

| | | | | Percent Specific Lysis of Targets: | | | |
|---|---|---|---|---|---|---|---|
| | | | E:T | | SVBalb | | MC57 |
| Vaccinia | DNA | DOTAP | Ratio | None | pV3 | p7 | p7 |
| VVT7 | p55gag | + | 40:1 | 4 | 6 | 66 | 3 |
| | | | 10:1 | 4 | 6 | 47 | 1 |
| | | | 2:1 | 5 | 4 | 23 | 2 |
| VVT7 | p55gag | – | 40:1 | 5 | 4 | 6 | 1 |
| | | | 10:1 | 6 | 4 | 6 | 1 |
| | | | 2:1 | 4 | 2 | 5 | 1 |
| VVwt | p55gag | + | 40:1 | 6 | 4 | 8 | 2 |
| | | | 10:1 | 1 | 1 | 1 | 1 |
| | | | 2:1 | 1 | 1 | 1 | 1 |
| VVgp160 | — | – | 40:1 | 4 | 4 | 52 | 3 |
| | | | 10:1 | 3 | 2 | 34 | 1 |
| | | | 2:1 | 5 | 4 | 15 | 1 |

Thus, an efficient system for nucleic acid immunization has been disclosed. Although preferred embodiments of the subject invention have been described in some detail, it is understood that obvious variations can be made without departing from the spirit and the scope of the invention as defined by the appended claims.

Deposits of Strains Useful in Practicing the Invention

A deposit of biologically pure cultures of the following strains was made with the American Type Culture Collection (ATCC), 12301 Parklawn Drive, Rockville, Md. The accession number indicated was assigned after successful viability testing, and the requisite fees were paid. The deposits were made under the provisions of the Budapest Treaty on the International Recognition of the Deposit of Microorganisms for the Purpose of Patent Procedure and the Regulations thereunder (Budapest Treaty). This assures maintenance of viable cultures for a period of thirty (30) years from the date of deposit. The organisms will be made available by the ATCC under the terms of the Budapest Treaty, and subject to an agreement between Chiron Corporation and the ATCC, which assures permanent and unrestricted availability of the progeny to one determined by the U.S. Commissioner of Patents and Trademarks to be entitled thereto according to 35 USC §122 and the Commissioner's rules pursuant thereto (including 37 CFR §1.12 with particular reference to 886 OG 638).

These deposits are provided merely as convenience to those of skill in the art, and are not an admission that a deposit is required under 35 USC §112. The nucleic acid sequences of these plasmids, as well as the amino acid sequences of the polypeptides encoded thereby, are controlling in the event of any conflict with the description herein. A license may be required to make, use, or sell the deposited materials, and no such license is hereby granted.

| Strain | Deposit Date | ATCC No. |
|---|---|---|
| pCMV6a120-SF2 in E. coli HB101 | March 8, 1990 | 68249 |
| pTM1-gp120 in E. coli HB101 | June 1, 1994 | 69638 |

What is claimed is:

1. A method of generating cytotoxic T-lymphocytes (CTLs) against a selected antigen, said method comprising:
   (a) introducing a source of bacteriophage T7 RNA polymerase into a cell of a vertebrate subject; and
   (b) transfecting said cell with a recombinant vector comprising a coding sequence which encodes said selected antigen operably linked to the bacteriophage T7 promoter, wherein said transfecting is done under conditions whereby said coding sequence is transcribed and translated in said cell in the presence of said T7 RNA polymerase, thereby resulting in the generation of CTLs against said antigen in said vertebrate subject.

2. The method of claim 1 wherein said T7 RNA polymerase is introduced into said cell using a viral vector which expresses a gene encoding said T7 RNA polymerase.

3. The method of claim 1 wherein said selected antigen is a viral antigen.

4. The method of claim 1 wherein said recombinant vector is encapsulated in a liposome preparation.

5. The method of claim 1 wherein said introducing is done prior to said transfecting.

6. The method of claim 1 wherein said introducing is done subsequent to said transfecting.

7. The method of claim 1 wherein said introducing is done concurrent with said transfecting.

8. The method of claim 1 wherein said T7 RNA polymerase is introduced into said cell using a vector which expresses a gene encoding said T7 RNA polymerase under the control of a T7 RNA polymerase promoter.

9. The method of claim 2 wherein said viral vector is derived from a poxvirus.

10. The method of claim 9 wherein said poxvirus is vaccinia virus.

11. The method of claim 9 wherein said poxvirus is an avipoxvirus.

12. The method of claim 3 wherein said viral antigen is a human immunodeficiency virus (HIV) envelope glycoprotein.

13. The method of claim 3 wherein said viral antigen is a hepatitis C virus (HCV) envelope glycoprotein.

14. The method of claim 12 wherein said HIV envelope glycoprotein is gp120.

15. The method of claim 13 wherein said HCV envelope glycoprotein is E2.

16. A method of generating cytotoxic T-lymphocytes (CTLs) against a selected viral antigen, said method comprising:
 (a) infecting a cell of a vertebrate subject with a vaccinia viral vector that expresses bacteriophage T7 RNA polymerase, to generate an infected cell;
 (b) transfecting said infected cell with a liposome-encapsulated recombinant vector comprising a coding sequence which encodes said selected viral antigen operably linked to the bacteriophage T7 promoter, wherein said transfecting is done under conditions whereby said coding sequence is transcribed and translated in said cell,
 thereby resulting in the generation of CTLs in said vertebrate subject against said selected viral antigen.

17. The method of claim 16 wherein said viral antigen is a human immunodeficiency virus (HIV) envelope glycoprotein.

18. The method of claim 16 wherein said viral antigen is a hepatitis c virus (HCV) envelope glycoprotein.

19. The method of claim 17 wherein said HIV envelope glycoprotein is gp120.

20. The method of claim 18 wherein said HCV envelope glycoprotein is E2.

* * * * *